United States Patent
Son et al.

(10) Patent No.: US 9,603,933 B2
(45) Date of Patent: *Mar. 28, 2017

(54) COMPOSITION FOR ENTERIC HARD CAPSULES, AND ENTERIC HARD CAPSULE PREPARED USING THE COMPOSITION

(75) Inventors: Jin Ryul Son, Incheon (KR); Hyon Ho Baek, Incheon (KR); Eun Hee Park, Incheon (KR); Sung Wan Lee, Incheon (KR); Min Gyu Song, Seoul (KR); Ja Hyun Cha, Incheon (KR); Jae Uk Cha, Seoul (KR); Won Hwa Ko, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/879,845

(22) PCT Filed: Feb. 21, 2011

(86) PCT No.: PCT/KR2011/001121
§ 371 (c)(1),
(2), (4) Date: Apr. 17, 2013

(87) PCT Pub. No.: WO2012/053703
PCT Pub. Date: Apr. 26, 2012

(65) Prior Publication Data
US 2013/0203868 A1    Aug. 8, 2013

(30) Foreign Application Priority Data
Oct. 21, 2010    (KR) .................. 10-2010-0103053

(51) Int. Cl.
*A61K 47/38*    (2006.01)
*A61K 9/48*    (2006.01)

(52) U.S. Cl.
CPC ............ *A61K 47/38* (2013.01); *A61K 9/4816* (2013.01)

(58) Field of Classification Search
CPC ...... A61K 47/38; A61K 47/36; A61K 9/4816; A61K 9/4825
See application file for complete search history.

(56) References Cited

U.S. PATENT DOCUMENTS

| | | |
|---|---|---|
| 4,138,013 A | 2/1979 | Okajima |
| 5,225,202 A | 7/1993 | Hodges et al. |
| 5,385,739 A | 1/1995 | Debregeas et al. |
| 5,540,945 A | 7/1996 | Ikushima |
| 5,733,575 A | 3/1998 | Mehra et al. |
| 6,346,269 B1 | 2/2002 | Hsiao et al. |
| 7,303,763 B2 | 12/2007 | Ho |
| 7,544,370 B2 | 6/2009 | Venkata Ramana Rao et al. |
| 7,550,153 B2 | 6/2009 | Venkata Ramana Rao et al. |
| 7,553,498 B2 | 6/2009 | Venkata Ramana Rao et al. |
| 7,585,283 B2 | 9/2009 | Kraizer et al. |
| 7,807,195 B2 | 10/2010 | Bhattacharya et al. |
| 7,838,027 B2 | 11/2010 | Venkata Ramana Rao et al. |
| 2007/0082046 A1 | 4/2007 | Chidambaram et al. |

FOREIGN PATENT DOCUMENTS

| | | |
|---|---|---|
| EP | 0056825 A1 | 8/1982 |
| EP | 1752140 A1 | 2/2007 |
| EP | 2223685 A1 | 9/2010 |
| EP | 2316454 A1 | 5/2011 |
| EP | 2316454 B1 | 9/2012 |
| EP | 2316454 B9 | 1/2013 |
| JP | 1976128421 | 11/1976 |
| JP | 1982142251 A | 9/1982 |
| JP | 2006016372 A | 1/2006 |

OTHER PUBLICATIONS

U.S. Pharmacopeia, Hypromellose Phthalate, NF Monographs: Hypromellose Phthalate, http://www.pharmacopeia.cn/v29240/usp29nf24s0_m39820.html, Jul. 11, 2014, pp. 1-2.
Written Opinion for International Application No. PCT/KR2011/001121 dated Nov. 25, 2011.
International Search Report for International Application No. PCT/KR2011/001121 dated Nov. 25, 2011.
By authority of the United States Pharmacopeial Convention Prepared by the Council of Experts and its Expert Committees, The United States Pharmacopeia, The National Formulary, May 1, 2011, USP 34, NF 29, vol. 1, pp. 1550-1551.
Pharmacopeial Forum, In-Process Revision, vol. 30(3) [May-Jun. 2004], pp. 984-985.
Japanese Office Action with Non-Final Rejection (excerpt) for Application No. 2013-534792 dated Aug. 21, 2014.
Al-Tabakha, Moawia M., HPMC Capsules: Current Status and Future Prospects, Journal of Pharmacy & Pharmaceutical Sciences 13(3), 2010, pp. 428-442.
Extended European Search Report for Application No. 11834503.2-1455 dated Oct. 12, 2015.

*Primary Examiner* — Jessica Worsham
(74) *Attorney, Agent, or Firm* — Cantor Colburn, LLP

(57) ABSTRACT

A composition for enteric hard capsules, and an enteric hard capsule prepared using the composition. The composition for enteric hard capsules may include polyol having at least three hydroxyl groups. During the storage of the enteric hard capsule prepared using the composition, the separation of salt from the capsule is delayed.

6 Claims, No Drawings

COMPOSITION FOR ENTERIC HARD CAPSULES, AND ENTERIC HARD CAPSULE PREPARED USING THE COMPOSITION

TECHNICAL FIELD

This application claims the benefit of Korean Patent Application No. 10-2010-00103053, filed on Oct. 21, 2010, in the Korean Intellectual Property Office, the disclosure of which is incorporated herein in its entirety by reference.

The present invention relates to a composition for enteric hard capsules, and an enteric hard capsule prepared using the composition. More particularly, the present invention relates to a composition for enteric hard capsules that includes polyol having at least three hydroxyl groups and an enteric hard capsule prepared using the composition.

BACKGROUND ART

Capsules for pharmaceutical preparations and neutraceutical preparations are generally prepared using gelatin, hydroxypropyl methylcellulose (HPMC) or hydroxypropyl methylcellulose phthalate (HPMCP) as base materials.

Gelatin capsules have high industrial productivity and high price competitiveness. However, if gelatin capsules contain 10 wt % moisture or less, they may lose plasticity and may show serious deterioration in impact resistance. Concern on mad cow disease has limited the use of gelatin capsules. For these reasons, plant-based HPMC capsules prepared without gelatin, and enteric HPMCP capsules have drawn attention.

However, conventional HPMCP capsules have low transparency and are fragile at a low moisture content of 10 wt % or less, for example. In addition, when being stored in severe high-temperature conditions, the HPMCP capsules may lose interior moisture slowly and harden because they include an excess of a neutralizing agent (e.g., alkaline agent). Furthermore, the neutralizing agent may separate from the hardened capsules, which is also called a separation of salt, within a relatively short period of time, mostly within 30 days.

DISCLOSURE OF INVENTION

Technical Problem

The present invention provides a composition for enteric hard capsules that includes polyol having at least three hydroxyl groups.

The present invention provides an enteric hard capsule prepared using the composition.

Solution to Problem

According to an aspect of the present invention, there is provided a composition for enteric hard capsules, the composition including: about 50 parts to about 90 parts by weight of hydroxypropyl methylcellulose phthalate (HPMCP); about 10 parts to about 50 parts by weight of hydroxypropyl methylcellulose (HPMC); about 5.5 to about 8.5 parts by weight of an alkaline agent; and about 2 parts to about 15 parts by weight of polyol having at least three hydroxyl groups, wherein the amounts of the HPMCP, the HPMC, the alkaline agent and the polyol in parts by weight are based on 100 parts by weight of the total weight of the HPMCP and the HPMC.

The HPMCP may include about 20 wt % to about 24 wt % of a methoxy group, about 6 wt % to about 10 wt % of a hydroxypropoxy group, and about 21 wt % to about 26 wt % of a phthalyl group, and may have a kinetic viscosity of about 48 cSt to about 66 cSt.

The alkaline agent may include at least one selected from the group consisting of ammonia, sodium hydroxide, potassium hydroxide, calcium hydroxide, and a mixture of at least two thereof.

The polyol having the at least three hydroxyl groups may include at least one selected from the group consisting of glycerin, sorbitol, triethanolamine, sucrose, and glycoside.

The composition may further include about 0.05 parts to about 0.5 parts by weight of an emulsifier based on 100 parts by weight of the total weight of the HPMCP and the HPMC.

The emulsifier may include at least one selected from the group consisting of sodium lauryl sulfate (SLS), sugar ester (SE), and a mixture of at least two thereof.

The compound may further include water, wherein the ratio (Ww/Wm) of the amount of water (Ww) to the total amount of the HPMCP and the HPMC (Wm) may be about 75 parts to about 85 parts by weight per about 15 parts to about 25 parts by weight.

According to another aspect of the present invention, there is provided an enteric hard capsule prepared using any one of the compositions described above.

Advantageous Effects of Invention

According to the one or more embodiments of the present invention, mechanically strong, highly transparent enteric hard capsules with a delayed separation of salt therefrom during storage may be prepared using the composition.

MODE FOR THE INVENTION

Hereinafter, a composition for enteric hard capsules, according to an embodiment of the present invention, will be described in detail.

According to the current embodiment of the present invention, the composition for enteric hard capsules may include: about 50 parts to about 90 parts by weight (for example, about 60 parts to about 80 parts by weight) of hydroxypropyl methylcellulose phthalate (HPMCP); about 10 parts to about 50 parts by weight (for example, about 20 parts to about 40 parts by weight) of hydroxypropyl methylcellulose (HPMC); about 5.5 parts to about 8.5 parts by weight (for example, about 6.0 parts to about 7.0 parts by weight) of an alkaline agent; and about 2 parts to about 15 parts by weight (for example, about 5 parts to about 10 parts by weight) of polyol having at least three hydroxyl groups (hereinafter, simply "the polyol", wherein the amounts of the HPMCP, the HPMC, the alkaline agent and the polyol in parts by weight are based on 100 parts by weight of the total weight of the HPMCP and the HPMC.

The HPMCP is not disintegrated at a pH of gastric juice (pH of about 1.2) for about 2 to about 4 hours, but is rapidly disintegrated at a pH of the small intestinal juice (pH of about 6.8) within 10 minutes. The HPMCP may include, for example, about 20 wt % to about 24 wt % of a methoxy group, about 6 wt % to about 10 wt % of a hydroxypropoxy group, and about 21 wt % to about 26 wt % of a phthalyl group. The amounts of the methoxy group, the hydroxypropoxy group and phthayl group in weight percentage are based on the total weight of the HPMCP, respectively. The HPMCP may have a kinetic viscosity of about 48 cSt (centistokes) to about 66 cSt. Throughout the specification, the terms "kinetic viscosity" and "viscosity" indicate the viscosity measured using an Anton-Paar MCR 301 (heating rate: 2° C./min, Spindle No.: CC 27 8009, RPM (shear rate): 1/s; available from Anton Paar), and specifically the term "kinetic viscosity of the HPMCP" indicates the viscosity of 20 wt % aqueous solution of the HPMCP measured as described above. When the composition for enteric hard capsules contains HPMCP having these physical characteristics, enteric hard capsules prepared using the composition may have good film strength, good transparency, and good elasticity. When the composition including the HPMCP is used to prepare enteric hard capsules, a less amount of the alkaline agent may be used. This may delay the separation of salt, which includes alkaline components, for example, $Na^+$, $K^+$, and $Ca^{2+}$, from capsule films during the storage of the enteric hard capsules. However, aspects of the present invention are not limited thereto. The HPMCP may have other physical properties different from the ones above. When the amount of the HPMCP is within the range of about 50 parts to about 90 parts by weight based on 100 parts by the total weight of the HPMCP and the HPMC, the aqueous composition may have a viscosity that is appropriate to form capsules with an appropriate thickness, and capsules formed from the aqueous composition may have good enteric characteristics.

The HPMC may improve elasticity of the fragile enteric capsule film and enteric capsule formability, and may enable to adjust the gelation start temperature of the aqueous composition to a temperature range of, for example, about 20° C. to about 70° C., applicable in commercial production. The HPMC may include about 4 wt % to about 12 wt %, for example, about 4 wt % to about 7.5 wt %, of hydroxypropoxy group, and about 19 to about 30 wt %, for example, about 27 wt % to about 30 wt %, of methoxy group. The amounts of the hydroxypropoxy group and the methoxy group in weight percentage are based on the total weight of the HPMC, respectively. The viscosity of 2 wt % aqueous solution of the HPMC may be from about 3 cps (centipoises) to about 50 cps, for example, from about 3 cps to about 15 cps. When the amount of the HPMC is within the range of about 10 parts to about 50 parts by the total weight based on 100 parts by weight of the HPMCP and the HPMC, the capsule formability may be good, and the resulting capsules may have good elasticity and good enteric characteristics.

The alkaline agent may solubilize the HPMCP, and may be an alkaline material such as ammonia, sodium hydroxide, potassium hydroxide, calcium hydroxide, or a mixture of at least two thereof. The alkaline agent may affect the gelation start temperature. As used herein, the term "gelation start temperature" indicates the temperature at which the viscosity of the aqueous composition that has declined with increasing temperatures during the viscosity measurement while heating begins to increase. When the amount of the alkaline agent is within the range of about 5.5 parts to about 8.5 parts by weight based on 100 parts by weight of the total weight of the HPMCP and the HPMC, the HPMCP may easily be solubilized, and the aqueous composition containing the alkaline agent may have an appropriate pH. The resulting capsules may also have good enteric characteristics, and the separation of salt from the capsule films may also be delayed during storage.

The polyol may improve the film strength of capsules, and improve the moisture retention characteristic of capsules to prevent hardening, and thus, to delay the separation of salts such as the alkaline agent from the capsules. That is, the polyol may serve as a plasticizer delaying the separation of salt from capsules. The polyol may include at least one selected from the group consisting of glycerin, sorbitol, triethanolamine, sucrose, and glycoside. When the amount of the polyol is within the range of about 2 parts to about 15 parts by weight based on 100 parts by weight of the total weight of the HPMCP and the HPMC, the resulting capsules may have appropriately plastic, soft films with appropriate moisture retention characteristic, and may have good transparency and strength. In addition, salts may not be separated from the capsules during storage for a long time.

In some embodiments, the composition for enteric hard capsules may further include about 0.05 parts to about 0.5 parts by weight (for example, about 0.1 parts to about 0.2 parts by weight) of an emulsifier based on 100 parts by weight of the total weight of the HPMCP and the HPMC. The emulsifier may improve capsule formability. The emulsifier may include sodium lauryl sulfate (SLS), sugar ester (SE), or a mixture thereof. In particular, the SLS may greatly improve the capsule formability. When the amount of the emulsifier is within the range of about 0.05 parts to about 0.5 parts by weight based on 100 parts by weight of the total weight of the HPMCP and the HPMC, the composition may have good capsule formability, and the resulting capsules also may have good quality and good safety in regards to gastroenteric disorders when dosed.

In some embodiments, the composition for enteric hard capsules may further include water. In this case, at least one of the HPMCP, the HPMC, the alkaline agent, the polyol and the emulsifier exist dissolved in water of the composition. The ratio (Ww/Wm) of the amount of water (Ww) to the total amount of the HPMCP and the HPMC (Wm) may be about 75 parts to about 85 parts by weight per about 15 parts to about 25 parts by weight.

According to another aspect of the present invention, there is provided an enteric hard capsule prepared using the composition described above.

Hereinafter, a method of preparing enteric hard capsules by using the composition, according to an embodiment of the present invention, will be described in detail. According to the current embodiment, the method may include the following steps:

A first step is to prepare a composition for enteric hard capsules by adding the HPMCP, the HPMC, the alkaline agent, the polyol and like to water at room temperature (for example, a temperature of about 20° C. to about 30° C.). As used herein, the term "composition" indicates a composition in which at least one of the HPMCP, the HPMC, the alkaline agent, and the polyol are at least partially dissolved in water, and/or at least partially gelled. The composition prepared as described above may have a pH of from about 4.5 to about 6.5, and a viscosity of from about 1000 cps to about 3000 cps, for example, from about 1500 cps to about 2500 cps, at room temperature. The gelation start temperature of the composition may vary depending on the mixing ratio of the HPMCP, the HPMC, the alkaline agent, and the polyol. For example, the gelation start temperature of the composition may be from about 40° C. to about 60° C.

The composition may further include at least one of titanium dioxide and other colorants, such as a mineral pigment, a natural pigment, or a tar pigment.

A second step is to heat the composition to a first temperature (i.e., gelation temperature) that is higher than the gelation start temperature thereof. The first temperature may be higher than the gelation start temperature of the composition by about 1° C. to about 20° C., for example, by about 5° C. to about 10° C.

A third step is to cool the heated composition to a second temperature (i.e., an immersion temperature) that is lower than the gelation start temperature of the composition. The second temperature may be lower than the gelation start temperature of the composition by about 15° C. to about 40° C., for example, by about 20° C. to about 35° C.

A fourth step is to immerse a mold pin heated to a third temperature that is higher than the gelation start temperature into the composition. The third temperature may be higher than the gelation start temperature of the composition by about 10° C. to about 40° C.

A fifth step is to remove the mold pin from the composition to obtain a film coated on the mold pin.

A sixth step is to maintain the film at a fourth temperature that is higher than the gelation start temperature for a first time period to fix the film onto the mold pin. The fourth temperature may be from about 60° C. to about 80° C. The first time period may be from about 1 minute to about 15 minutes, for example, about 8 minutes.

A seventh step is to dry the fixed film at a fifth temperature for a second time period to obtain a capsule shell. The fifth temperature may be from about 20° C. to about 40° C., and the second time period may be from about 30 minutes to about 60 minutes.

Hereinafter, one or more embodiments will be described in detail with reference to the examples below. These examples are for illustrative purposes only and are not intended to limit the scope of the invention.

EXAMPLES

Examples 1-9 & Comparative Examples 1-7

Preparation of Compositions

A HPMCP, a HPMC, NaOH, a plasticizer, an emulsifier, and water were mixed in appropriate ratios shown in Table 1 to prepare compositions for enteric hard capsules. The compositions were maintained at a temperature of 20° C.

TABLE 1

| | Compositions (parts by weight)*[1] | | | | | | | | | | | | |
|---|---|---|---|---|---|---|---|---|---|---|---|---|---|
| | HPMCP | | HPMC | | | Alkaline Agent | | | Platicizer | | | | Emulsifier |
| | HP-50*[2] | HP-55*[3] | HPMC 2906*[4] | HPMC 2910*[5] | HPMC 2208*[6] | Na—OH | Ca—(OH)$_2$ | KOH | Glycerin | Sorbitol | PG*[7] | PEG*[8] | SLS |
| Example 1 | 80 | 0 | 20 | 0 | 0 | 7.0 | 0 | 0 | 5 | 0 | 0 | 0 | 0.1 |
| Example 2 | 80 | 0 | 20 | 0 | 0 | 7.0 | 0 | 0 | 10 | 0 | 0 | 0 | 0.1 |
| Example 3 | 80 | 0 | 20 | 0 | 0 | 7.0 | 0 | 0 | 15 | 0 | 0 | 0 | 0.1 |
| Example 4 | 80 | 0 | 20 | 0 | 0 | 7.0 | 0 | 0 | 2 | 0 | 0 | 0 | 0.1 |
| Example 5 | 80 | 0 | 0 | 0 | 20 | 0 | 4.5 | 0 | 7 | 0 | 0 | 0 | 0.1 |
| Example 6 | 80 | 0 | 0 | 20 | 0 | 0 | 0 | 8.5 | 12 | 0 | 0 | 0 | 0.1 |
| Example 7 | 80 | 0 | 20 | 0 | 0 | 7.0 | 0 | 0 | 0 | 5 | 0 | 0 | 0.1 |
| Example 8 | 80 | 0 | 20 | 0 | 0 | 7.0 | 0 | 0 | 0 | 10 | 0 | 0 | 0.1 |
| Example 9 | 0 | 80 | 20 | 0 | 0 | 8.5 | 0 | 0 | 10 | 0 | 0 | 0 | 0 |
| Comparative Example 1 | 80 | 0 | 20 | 0 | 0 | 7.0 | 0 | 0 | 0 | 0 | 5 | 0 | 0.1 |
| Comparative Example 2 | 80 | 0 | 20 | 0 | 0 | 7.0 | 0 | 0 | 0 | 0 | 10 | 0 | 0.1 |
| Comparative Example 3 | 80 | 0 | 20 | 0 | 0 | 7.0 | 0 | 0 | 0 | 0 | 0 | 5 | 0.1 |
| Comparative Example 4 | 80 | 0 | 20 | 0 | 0 | 7.0 | 0 | 0 | 0 | 0 | 0 | 10 | 0.1 |
| Comparative Example 5 | 80 | 0 | 20 | 0 | 0 | 7.0 | 0 | 0 | 1 | 0 | 0 | 0 | 0.1 |
| Comparative Example 6 | 0 | 80 | 20 | 0 | 0 | 8.5 | 0 | 0 | 0 | 0 | 0 | 0 | 0.1 |
| Comparative Example 7 | 0 | 80 | 20 | 0 | 0 | 8.5 | 0 | 0 | 0.5 | 0 | 0 | 0 | 0.1 |

*[1]In the composition, the amount of water is 4 times more than the total weight of the HPMCP and the HPMC.
*[2]HPMCP HP-50 (containing 22.3 wt % of a methoxy group, 8.5 wt % of a hydroxypropoxy group, and 25.21 wt % of a phthalyl group; and having a kinetic viscosity of 54.3 cSt), produced by Samsung Fine Chemicals Co., Ltd.
*[3]HPMCP HP-55 (containing 19.8 wt % of a methoxy group, 7.1 wt % of a hydroxypropoxy group, and 33.15 wt % of a phthalyl group; and having a kinetic viscosity of 42.97 cSt), produced by Samsung Fine Chemicals Co., Ltd.
*[4]AnyCoat-C BN4, produced by Samsung Fine Chemicals Co., Ltd.
*[5]AnyCoat-C AN4, produced by Samsung Fine Chemicals Co., Ltd.
*[6]AnyCoat-C CN4, produced by Samsung Fine Chemicals Co., Ltd.
*[7]Propylene glycol
*[8]Polyethylene glycol (Preparation of Enteric Capsules)

Enteric capsules were prepared using each of the compositions prepared above according to the following method according to the conditions shown in Table 2.

First, each of the compositions was heated to a gelation temperature thereof. Then, the composition was cooled to a temperature (immersion temperature) lower than the gelation start temperature of the composition. Then, a mold pin (Technophar Equipment & Service Ltd., pin, #0) preheated to a temperature (mold pin temperature) that is higher than the gelation start temperature of the corresponding composition was immersed in the composition (herein, the composition before being gelated) so that the mold pin was coated with the composition. During this step, the composition coated on the mold pin was at least partially gelated. Then, the mold pin was removed from the composition. Subsequently, the mold pin coated with the composition was maintained at a temperature of 70° C. for about 5 minutes and was then dried at a temperature of 30° C. for about 45 minutes.

TABLE 2

| | Gel Forming Conditions *1 | | | |
|---|---|---|---|---|
| | Gelation Start Temperature (° C.) | Gelation Temperature (° C.) | Immersion temperature (° C.) | Mold Pin Temperature (° C.) |
| Example 1 | 46 | 65 | 26 | 80 |
| Example 2 | 46 | 65 | 26 | 80 |
| Example 3 | 46 | 65 | 26 | 80 |
| Example 4 | 46 | 65 | 26 | 80 |
| Example 5 | 52 | 70 | 26 | 80 |
| Example 6 | 50 | 70 | 28 | 82 |
| Example 7 | 46 | 65 | 26 | 80 |
| Example 8 | 46 | 65 | 26 | 80 |
| Example 9 | 47 | 64 | 28 | 82 |
| Comparative Example 1 | 46 | 65 | 26 | 80 |
| Comparative Example 2 | 46 | 65 | 26 | 80 |
| Comparative Example 3 | 46 | 65 | 26 | 80 |
| Comparative Example 4 | 46 | 65 | 26 | 80 |
| Comparative Example 5 | 46 | 65 | 26 | 80 |
| Comparative Example 6 | 45 | 65 | 28 | 82 |
| Comparative Example 7 | 45 | 65 | 28 | 82 |

*1: In Examples 1-9, capsules were prepared using a hot-pin process, which is a kind of thermal gelation.

Evaluation Example 1

Characteristics of capsules prepared according to Examples 1-9 and Comparative Examples 1-7 were evaluated as follows. The results are shown in Table 3.

<Impact Test>

Twenty capsules from each example underwent impact by dropping in free fall a 70 g weight poise from a 10 cm height. Then, the number of broken capsules among the 20 tested capsules was counted. The tested capsules had a moisture content of about 8±0.5 wt %.

<Salt Separation Test>

Five capsules from each example were put in each vial, and the vials, remained open, were placed in a Life Tester (JEIO TECH, TH-G-180L) at a temperature of about 40° C. and a relative humidity of about 75%. Then, the appearances of the capsules were observed once a day over four months. The days from when the test began to when salt began to separate from the capsules were recorded.

<Transparency>

While each dried-out capsule was held against a fluorescent light, turbidity of the capsule was graded by visual inspection to one of three following categories.

⊙: clear
○: slightly unclear (if capsule surface appears slightly rough or if undissolved impurities are seen)
Δ: hazy Evaluation Example 2

A disintegration test was performed according to the Korean Pharmacopoeia IX ($9^{th}$ ed). Capsules prepared according to Examples 1-9 and Comparative Examples 1-7 were immersed in a test solution at a pH of 1.2, similar to the pH of gastric juice, and in a test solution at a pH of 6.8, similar to the pH of the small intestinal juice, to measure disintegration time. The results are shown in Table 3.

TABLE 3

| | Impact Test | Time when Salt Separation occurred (days) | Transparency | Disintegration Test Disintegration Time (min) | |
|---|---|---|---|---|---|
| | | | | pH 1.2 | pH 6.8 |
| Example 1 | 0 | Not Occurred | ⊙ | >120 | 3.20 |
| Example 2 | 0 | Not Occurred | ⊙ | >120 | 3.35 |
| Example 3 | 0 | Not Occurred | ⊙ | >120 | 3.48 |
| Example 4 | 0 | 65 | ⊙ | >120 | 3.16 |
| Example 5 | 0 | Not Occurred | ⊙ | >120 | 3.28 |
| Example 6 | 0 | Not Occurred | ⊙ | >120 | 3.11 |
| Example 7 | 4 | Not Occurred | ○ | >120 | 3.24 |
| Example 8 | 4 | Not Occurred | ○ | >120 | 3.79 |
| Example 9 | 4 | Not Occurred | ○ | >120 | 3.88 |
| Comparative Example 1 | 0 | 30 | ⊙ | >120 | 3.04 |
| Comparative Example 2 | 0 | 35 | ⊙ | >120 | 2.99 |
| Comparative Example 3 | 0 | 28 | ⊙ | >120 | 3.15 |
| Comparative Example 4 | 0 | 41 | ⊙ | >120 | 3.33 |
| Comparative Example 5 | 0 | 26 | ⊙ | >120 | 3.45 |
| Comparative Example 6 | 4 | 20 | ○ | >120 | 3.16 |
| Comparative Example 7 | 5 | 21 | ○ | >120 | 3.40 |

Referring to Table 3, in the capsules of Examples 1-9 the separation of salt is further delayed than in the capsules of Comparative Examples 1-7. The capsules of Examples 1-9 are also better than or similar to those of Comparative Examples 1-7 in terms of impact resistance and transparency. The capsules prepared according to Examples 1-9 and Comparative Examples 1-7 do not disintegrate for at least 2 hours in the gastric juice conditions, but disintegrate within 4 minutes in the small intestinal juice condition. This indicates that the capsules of Examples 1-9 and Comparative Examples 1-7 all have enteric characteristics.

While the present invention has been particularly shown and described with reference to exemplary embodiments thereof, it will be understood by those of ordinary skill in the art that various changes in form and details may be made therein without departing from the scope of the present invention as defined by the following claims.

The invention claimed is:
1. A composition for enteric hard capsules, the composition comprising:
about 50 parts to about 90 parts by weight of hydroxypropyl methylcellulose phthalate (HPMCP), wherein the HPMCP includes about 20 wt % to about 24 wt % of a methoxy group, about 6 wt % to about 10 wt % of a hydroxypropoxy group, and about 21 wt % to about 26 wt % of a phthalyl group, and has a kinetic viscosity of about 48 cSt to about 66 cSt;

about 10 parts to about 50 parts by weight of hydroxypropyl methylcellulose (HPMC);

about 5.5 to about 8.5 parts by weight of an alkaline agent; and about 5 parts to about 15 parts by weight of a polyol having at least three hydroxyl groups, wherein the amounts of the HPMCP, the HPMC, the alkaline agent and the polyol in parts by weight are based on 100 parts by weight of the total weight of the HPMCP and the HPMC, wherein the polyol serves as a plasticizer delaying the separation of salts from a capsule prepared from the composition, and wherein the polyol having the at least three hydroxyl groups comprises glycerin.

2. The composition of claim 1, wherein the alkaline agent comprises at least one selected from the group consisting of ammonia, sodium hydroxide, potassium hydroxide, calcium hydroxide, and a mixture of at least two thereof.

3. The composition of claim 1, further comprising about 0.05 parts to about 0.5 parts by weight of an emulsifier based on 100 parts by weight of the total weight of the HPMCP and the HPMC.

4. The composition of claim 3, wherein the emulsifier comprises at least one selected from the group consisting of sodium lauryl sulfate (SLS), sugar ester (SE), and a mixture of at least two thereof.

5. The compound of claim 1, further comprising water, wherein the ratio (Ww/Wm) of the amount of water (Ww) to the total amount of the HPMCP and the HPMC (Wm) is about 75 parts to about 85 parts by weight per about 15 parts to about 25 parts by weight.

6. An enteric hard capsule prepared using the composition of claim 1.

* * * * *